United States Patent [19]

Kuroda et al.

[11] Patent Number: 4,861,691
[45] Date of Patent: Aug. 29, 1989

[54] ELECTROPHOTOGRAPHIC PHOTOSENSITIVE MATERIAL CONTAINING HYDRAZONE COMPOUND

[75] Inventors: Masami Kuroda; Yoichi Nakamura; Noboru Furusho, all of Kanagawa, Japan

[73] Assignee: Fuji Electric Company, Ltd., Kanagawa, Japan

[21] Appl. No.: 137,212

[22] Filed: Dec. 22, 1987

[30] Foreign Application Priority Data

Dec. 22, 1986 [JP] Japan ................. 61-305652
Dec. 29, 1986 [JP] Japan ................. 61-310176
Jan. 27, 1987 [JP] Japan ................. 62-16764

[51] Int. Cl.$^4$ ............................................. G03G 5/14
[52] U.S. Cl. ................................... 430/59; 430/73
[58] Field of Search .................. 430/59, 70, 71, 72, 430/73, 77, 74

[56] References Cited

U.S. PATENT DOCUMENTS 3,242,188 3/1966 Siegrist et al. ................... 430/77
4,554,231 11/1985 Ishikawa et al. .................. 430/59

Primary Examiner—John L. Goodrow
Attorney, Agent, or Firm—Sughrue, Mion, Zinn, Macpeak & Seas

[57] ABSTRACT

An electrophotographic photosensitive material is disclosed, wherein the electrophotographic photosensitive material comprises a photosensitive layer containing at least one hydrazone compound selected from the group consisting of compounds having the general formulae (I) and (II):

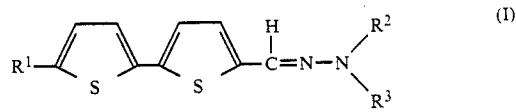

wherein $R^1$ is a hydrogen or halogen atom or an alkyl group, an alkoxy group, a nitro group, an acyl group or an amino group and $R^2$ and $R^3$ each represents a substituted or unsubstituted alkyl group, or a substituted or unsubstituted aryl group;

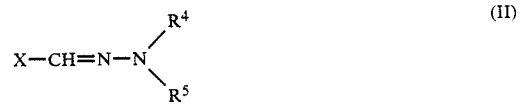

wherein $R^4$ and $R^5$ each represents a substituted or unsubstituted alkyl group, or a substituted or unsubstituted aryl group and X is a group of the formula

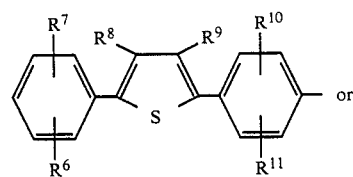 or

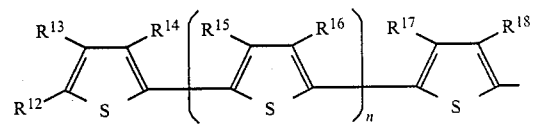

in which $R^6$ to $R^{18}$ each represents a hydrogen or halogen atom or a hydroxy group, an alkyl group, an alkoxy group, an allyl group, an acyl group, an acyloxy group, an alkoxycarbonyl group, an aryl group, a cyano group, a nitro group, an amino group, an alkylamino group or an arylamino group and n is an integer of 1, 2, 3, 4 or 5.

9 Claims, 1 Drawing Sheet

ELECTROPHOTOGRAPHIC PHOTOSENSITIVE MATERIAL CONTAINING HYDRAZONE COMPOUND

FIELD OF THE INVENTION

This invention relates to an electrophotogrpahic photosensitive material. More particularly, it relates to an electrophotographic photosensitive material which contains a specific hydrazone compound in the photosensitive layer formed on an electroconductive substrate.

BACKGROUND OF THE INVENTION

Photosensitive materials so far used in electrophotographic photosensitive materials (hereinafter also referred to as photosensitive materials) include inorganic photoconductive substances, such as selenium and selenium alloys, dispersions of inorganic photoconductive substances, such as zinc oxide and cadmium sulfide, in resin binders, organic photoconductive substances, such as poly-N-vinylcarbazole and polyvinyl-anthracene, organic photoconductive substances, such as phthalocyanine compounds and bisazo compounds, and dispersions of such organic photoconductive substances in resin binders.

Photosensitive materials are required to have the function of holding surface charges in the dark, the functon of receiving light and generating charges and the function of receiving light and transporting charges. There are two kinds of photosensitive materials, namely the so-called monolayer type photosensitive material consisting of one single layer having all the three functions and the so-called laminate type photosensitive material composed of functionally distinguishable layers, namely a layer which contributes mainly to charge generation and a layer which contributes mainly to retention of surface charges in the dark and charge transport upon receiving light. In electrophotographic image formation using these photosensitive materials, the technique of Carlson, for example, is applied. Image formation by this technique includes charging of the photosensitive material by corona discharge in the dark, formation of latent electrostatic images (e.g. letters, pictures) by illumination of the charged photosensitive material surface, development of the latent electrostatic images thus formed with a toner and fixation of the developed toner images on a supporting material, such as a paper sheet, following transfer thereto. After toner image transfer, the photosensitive material is subjected to the steps of charge removal, removal of remaining toner (cleaning), neutralization of residual charge by means of light (erasure), and so on, and then submitted to reuse.

In recent years, electrophotographic photosensitive materials in which organic materials are used have been put to practical use because of their advantageous features such as flexibility, thermal stability and film forming property. Thus, for example, there may be mentioned photosensitive materials comprising poly-N-vinylcarbazole and 2,4,7-trinitrofluoren-9-one (described in U.S. Pat. No. 3,484,237), photosensitive materials in which an organic pigment is used as the main component (described in Japanese Patent Application (OPI) No. 37543/1972) (the term "OPI" as used herein means "unexamined published Japanese Patent Application") and photosensitive materials in which a eutectic complex is used as the main component (Japanese Patent Application (OPI) No. 10735/1972). A number of novel hydrazone compounds have also been put to practical use.

However, although organic materials have a number of advantageous features as compared with inorganic materials, none of organic materials can fully meet all requirements set forth with respect to the characteristic properties of photosensitive materials for electrophotography. Organic materials are still unsatisfactory particularly in respect of photosensitivity and of characteristics at the time of continuous repeated use.

SUMMARY OF THE INVENTION

Accordingly, it is an object of the invention, which has been made in view of the foregoing, to provide a photosensitive material for use in electrophotographic copies and printers, which has high sensitivity and shows good characteristics in repeated use, through the use, as a charge transporting substance in the photosensitive layer, of a novel organic material that has not yet been used.

In accordance with the invention, the above object is achieved by using an electrophotographic photosensitive material which has a photosensitive layer containing at least one hydrazone compound selected from the group consisting of the following structural formulas (I) and (II):

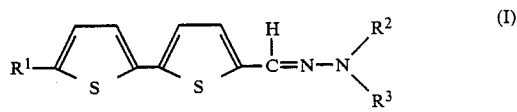

wherein $R^1$ is a hydrogen or halogen atom or an alkyl group, an alkoxy group, a nitro group, an acyl group or an amino group and $R^2$ and $R^3$ each represents a substituted or unsubstituted alkyl group or a substituted or unsubstituted aryl group;

wherein $R^4$ and $R^5$ each represents a substituted or unsubstituted alkyl group or a substituted or unsubstituted aryl group and X is a group of the formula

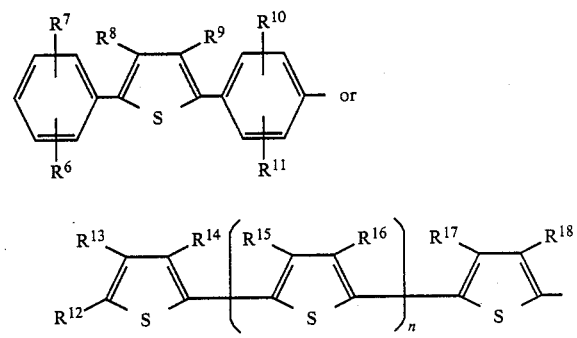

wherein $R^6$ to $R^{18}$ each represents a hydrogen or halogen atom or a hydroxy group, an alkyl group, an alkoxy group, an allyl group, an acyl group, an acyloxy group, an alkoxycarbonyl group, an aryl group, a cyano group, a nitro group, an amino group, an alkylamino group or an arylamino group and n is an integer of 1, 2, 3, 4 or 5.

Figure 1:
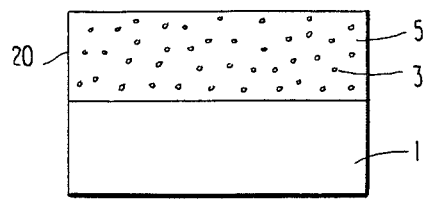
FIGS. 1–3 each is a schematic cross-sectional representation of a photosensitive material of the invention.

The three embodiments shown differ in mode from one another. In the figures, an electroconductive substrate is indicated by reference number 1, a charge generating substance by 3, a charge generating layer by 4, a charge transporting substance by 5, a charge transporting layer by 6, a covering layer by 7, and a photosensitive layer by 20, 21 or 22.

DETAILED DESCRIPTION OF THE INVENTION the formula (I), the alkyl group represented by $R^1$ is preferably an alkyl group having from 1 to 10 carbon atoms, and more preferably from 1 to 5 carbon atoms, for example, a methyl group, an ethyl group, a propyl group, or a butyl group, etc.; the alkoxy group represented by $R^1$ is preferably an alkoxy group having from 1 to 10 carbon atoms, and more preferably from 1 to 5 carbon atoms, for example, a methoxy group, an ethoxy group, a propoxy group, etc.; the amino group represented by $R^1$ is an amino group having from 0 to 10 carbon atoms, and more preferably from 0 to 6 carbon atoms, for example, an amino group, a diethylamino group, etc.; and the acyl group represented by $R^1$ is preferably an acyl group having from 1 to 6 carbon atoms, and more preferably from 1 to 3 carbon atoms, for example, a formyl group, an acetyl group, a propionyl group, etc.; the halogen atom represented by $R^1$ is preferably a chlorine atom; bromine atom, etc.

The alkyl group represented by $R^2$ and $R^3$ is preferably an alkyl group having from 1 to 10 carbon atoms, and more preferably from 1 to 5 carbon atoms, for exmaple, a methyl group, an ethyl group, a propyl group, etc.; the aryl group represented by $R^2$ and $R^3$ is preferably an aryl group having from 6 to 12 carbon atoms, for example, a phenyl group, a naphthyl group, etc.

Examples of preferred substituent of the substituted alkyl group represented by $R^2$ and $R^3$ include an aryl group preferably having from 6 to 12 carbon atoms; an alkoxy group preferably having from 1 to 5 carbon atoms; and a halogen atom, such as a chlorine atom, a bromine atom, etc.

Examples of preferred substituent of the substituted aryl group represented by $R^2$ and $R^3$ include an alkyl group preferably having from 1 to 5 carbon atoms; an alkoxy group preferably having from 1 to 5 carbon atoms; and a halogen atom such as a chlorine atom, a bromine atom, etc.

$R^2$ and $R^3$ may be the same or different.

In the formula (II), the alkyl group represented by $R^4$ and $R^5$ is preferably an alkyl group having from 1 to 10 carbon atoms, and more preferably having from 1 to 5 carbon atoms, for example, a methyl group, an ethyl group, a propyl group, etc. The aryl group represented by $R^4$ and $R^5$ is preferably an aryl group having from 6 to 12 carbon atoms, for example, a phenyl group, a naphthyl group, etc.

Examples of the substituents of the substituted alkyl group and the substituted aryl group represented by $R^4$ and $R^5$ include the same as those represented by $R^2$ and $R^3$.

The alkyl group represented by $R^6$ to $R^8$ is preferably an alkyl group having from 1 to 10 carbon atoms, and more preferably having from 1 to 5 carbon atoms, for example, a methyl group, an ethyl group, a propyl group, etc.; the halogen atom represented by $R^6$ to $R^{18}$ is preferably a chlorine atom, a bromine atom, etc.; the alkoxy group represented by $R^6$ to $R^{18}$ is preferably an alkoxy group having from 1 to 10 carbon atoms and more preferably having from 1 to 5 carbon atoms, for example, a methoxy group, an ethoxy group, a propoxy group, etc.; the acyl group represented by $R^6$ to $R^{18}$ is preferably an acyl group having from 1 to 10 carbon atoms, and more preferably from 1 to 5 carbon atoms, for example, a formyl group, an acetyl group, a propionyl group, etc.; the acyloxy group represented by $R^6$ to $R^{18}$ is preferably an acyloxy group having from 1 to 10 carbon atoms, and more preferably from 1 to 5 carbon atoms, for example, a carboxy group, an acetoxy group, a propionyloxy group, etc.; the alkoxycarbonyl group represented by $R^6$ to $R^{18}$ is preferably an alkoxycarbonyl group having from 2 to 10 carbon atoms, and more preferably from 2 to 5 carbon atoms, for example, a methoxycarbonyl group, an ethoxycarbonyl group, etc.; the aryl group represented by $R^6$ to $R^{18}$ is preferably an aryl group having from 6 to 12 carbon atoms, for example, a phenyl group, a naphthyl group, etc.; the alkylamino group is preferably a dialkyl amino group wherein the alkyl moiety has from 1 to 5 catbon atoms, for example, dimethyl amino group, diethylamino group, etc.; the arylamino group is preferably a diarylamino group having from 6 to 12 carbon atoms, for example, diphenylamino group, etc.

Further, $R^6$ to $R^{18}$ in the formula (II) each may be substituted by an alkoxy group having from 1 to 5 carbon atoms, an alkyl group having from 1 to 5 carbon atoms, an aryl group having from 6 to 12 carbon atoms. and a halogen atom such as a chlorine atom and a bromine atom.

As for the use of the hydrazone compounds represented by the general formulas (I) and (II) in photosensitive layers, there has been no precedent before.

In the course of their intensive study of various organic materals as made in an attempt to achieve the above object, the present inventors conducted a number of experiments with those hydrazone compounds and, as a result, found that the use of such specific hydrazone compounds represented by the above general formulas (I) and (II) as charge transporting substances is very effective in improving electrophotographic characteristics, although the fact has not been given a satisfactory technical explanation as yet. Based on this finding, they obtained photosensitive materials having high sensitivity and good repeated-use characteristics.

The hydrazone compounds of general formulas (I) and (II) to be used in accordance with the invention can be synthesized in the conventional manner by reacting the corresponding aldehyde and hydrazine in an appropriate organic solvent, such as an alcohol, if necessary in the presence of an acid (condensing agent).

Typical examples of the thus-obtainable hydrazone compounds of general formulas (I) and (II) are given below.

The following compounds No. I-1 to No. I-32 are typical examples of the compound of general formula (I):

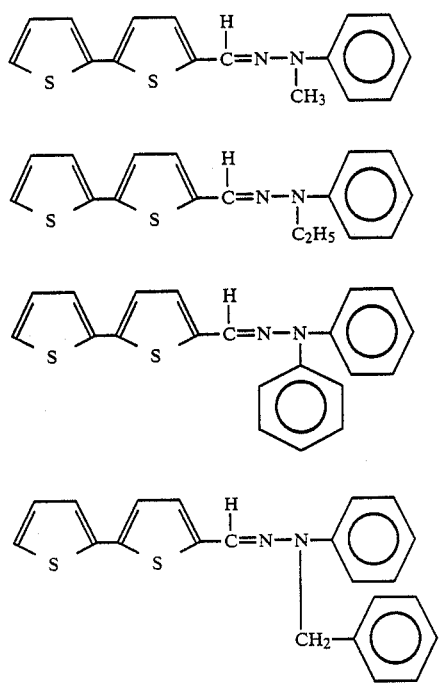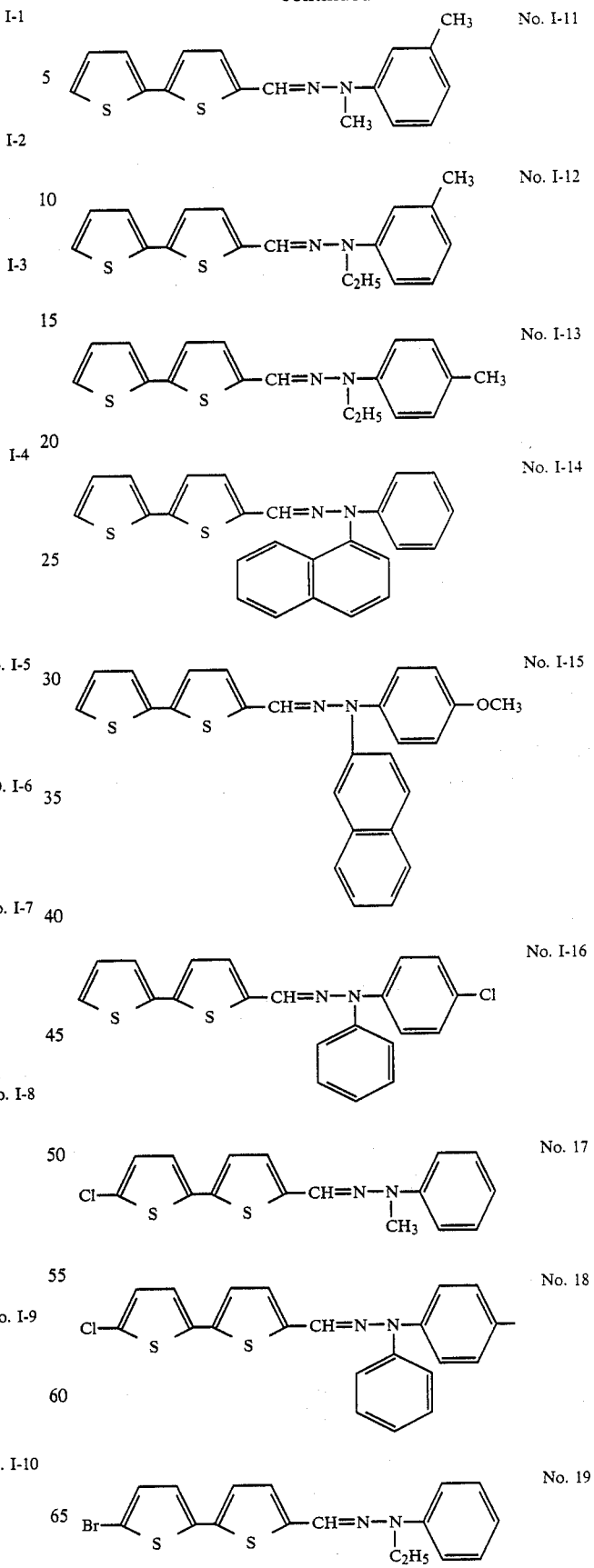

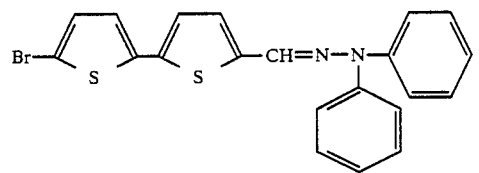  No. I-20
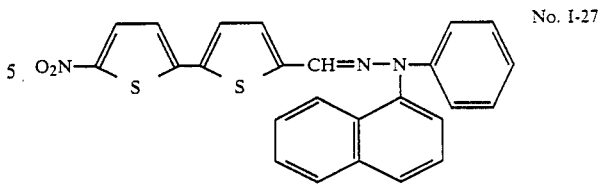  No. I-27
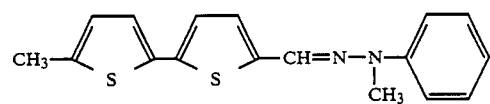  No. I-21
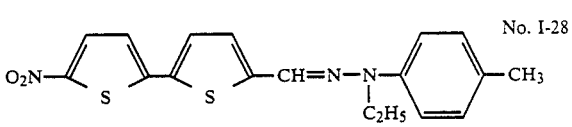  No. I-28
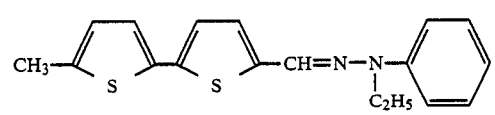  No. I-22
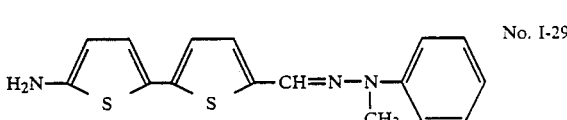  No. I-29
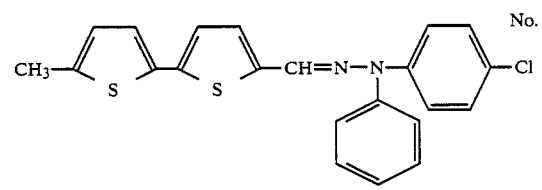  No. I-23
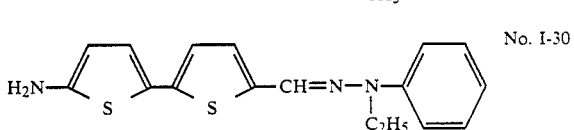  No. I-30
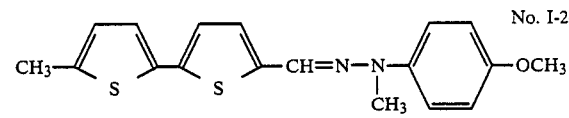  No. I-24
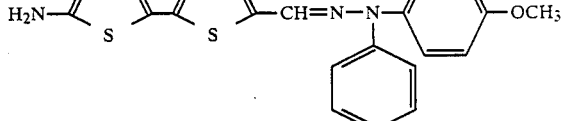  No. I-31
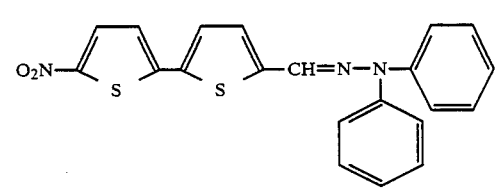  I-25
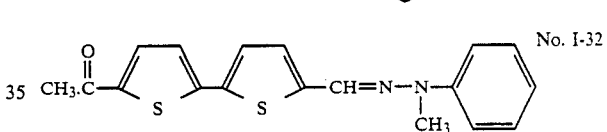  No. I-32
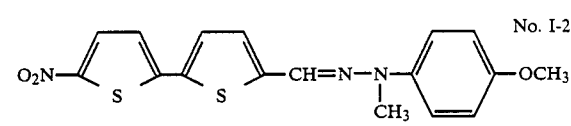  No. I-26
The following compounds No. II-1 to No. II-42 are typical examples of the compound of general formula (II);
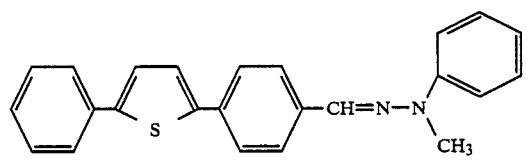  Compound No. II-1
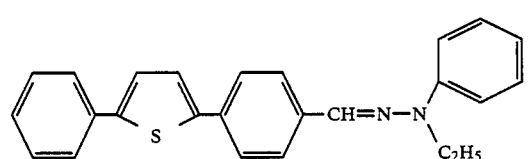  No. II-2
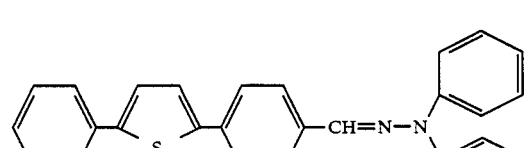  No. II-3

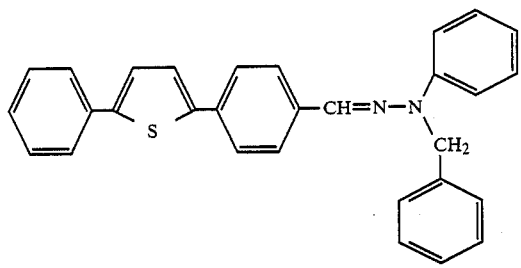
No. II-4
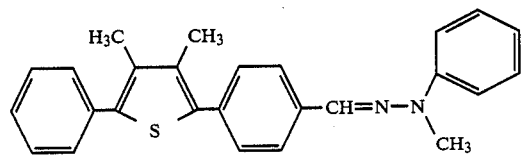
No. II-5
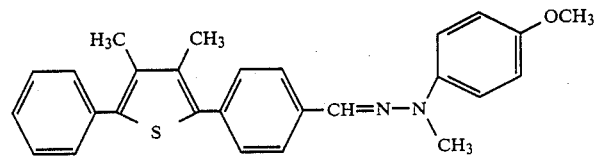
No. II-6
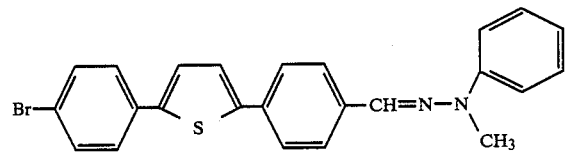
No. II-7
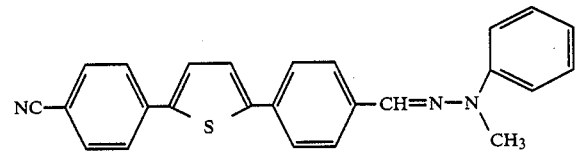
No. II-8
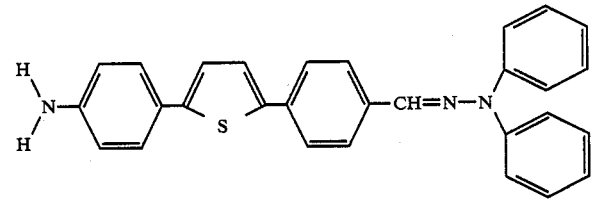
No. II-9
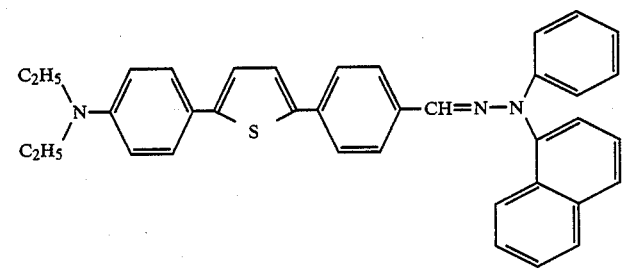
No. II-10
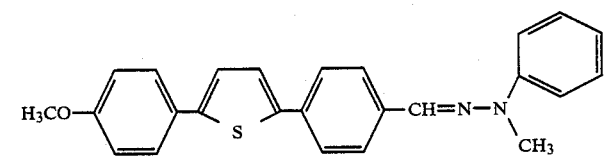
No. II-11

-continued
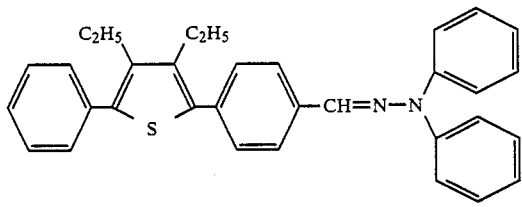 No. II-12
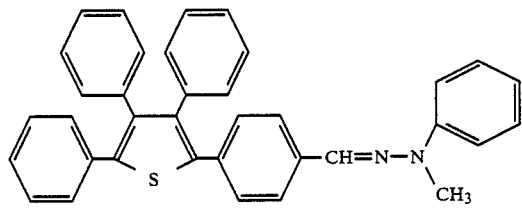 No. II-13
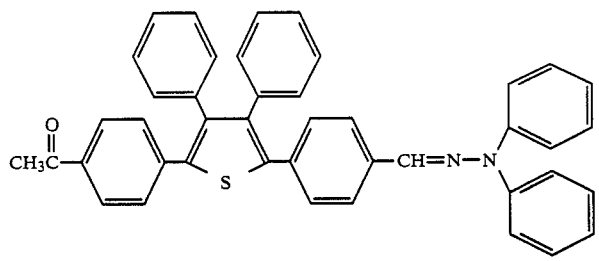 No. II-14
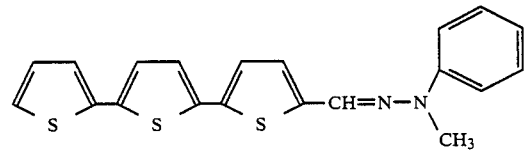 No. II-15
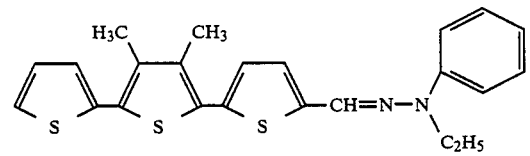 No. II-16
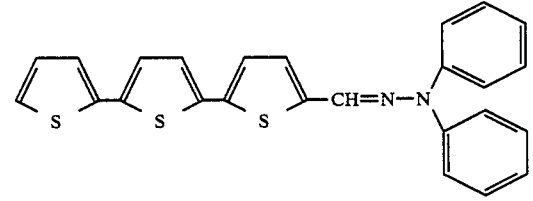 No. II-17
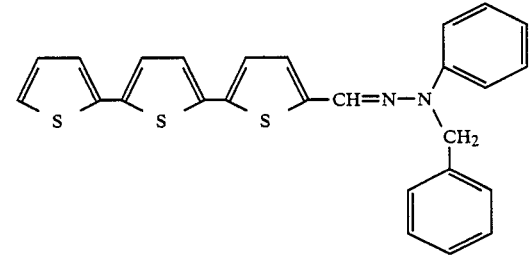 No. II-18

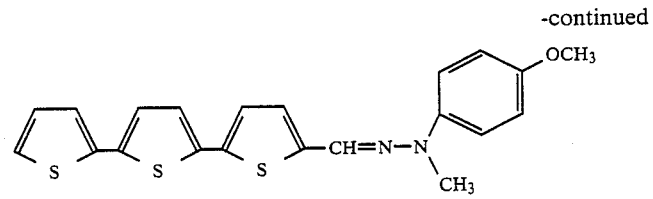
No. II-19
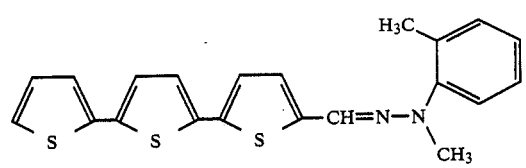
No. II-20
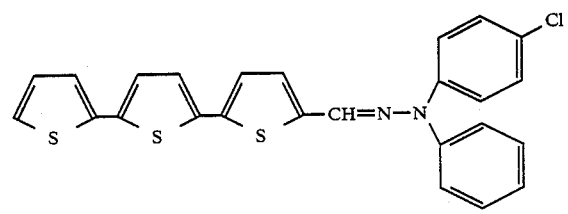
No. II-21
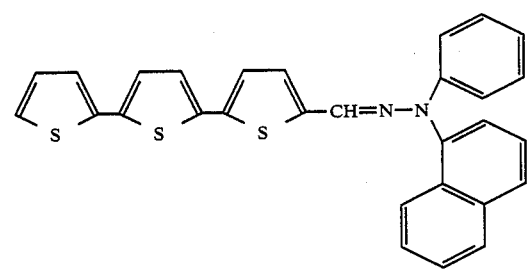
No. II-22
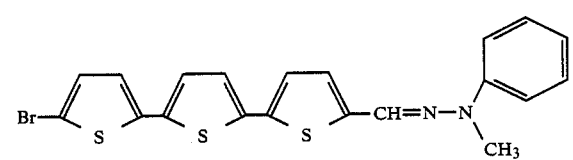
No. II-23
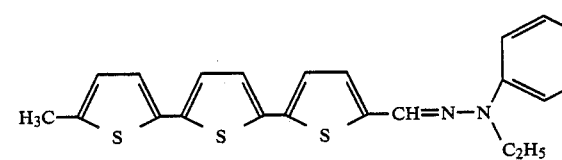
No. II-24
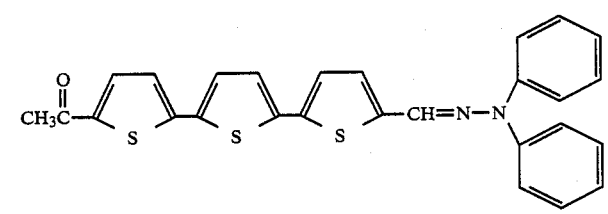
No. II-25
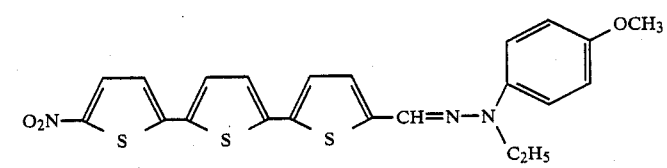
No. II-26

-continued
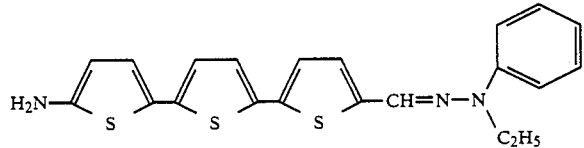
No. II-27
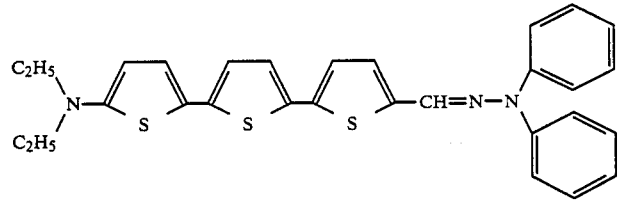
No. II-28
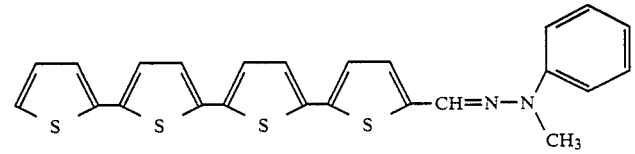
No. II-29
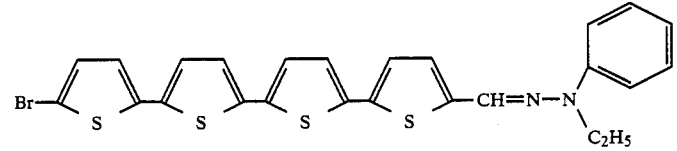
No. II-30
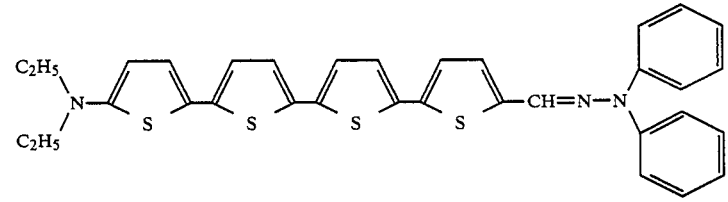
No. II-31
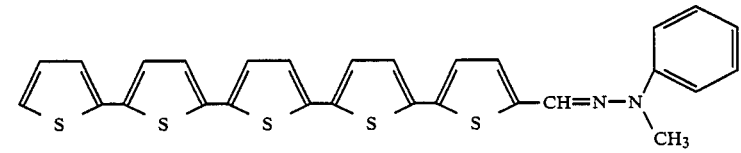
No. II-32
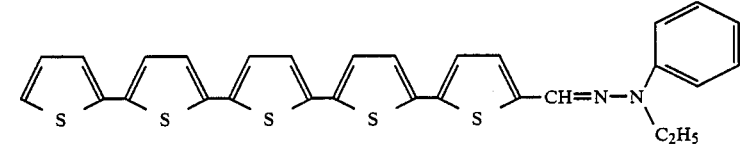
No. II-33
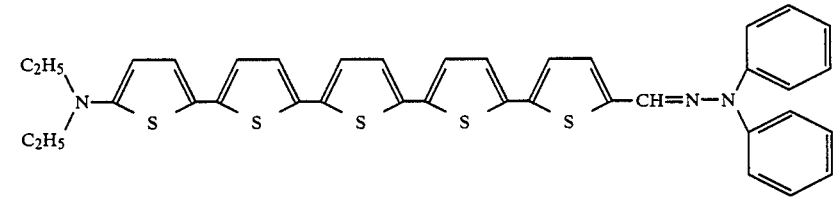
No. II-34

-continued

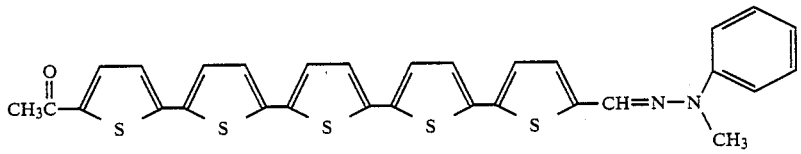
No. II-35

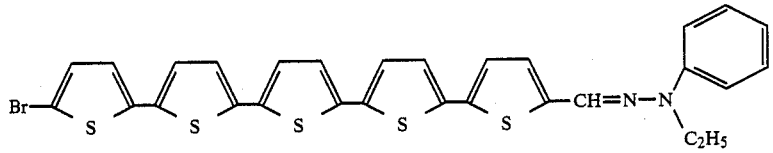
No. II-36

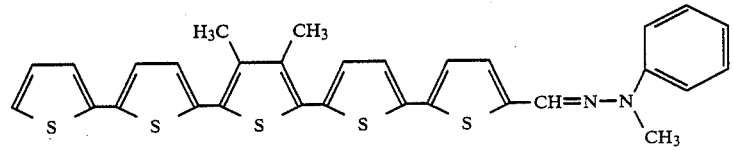
No. II-37

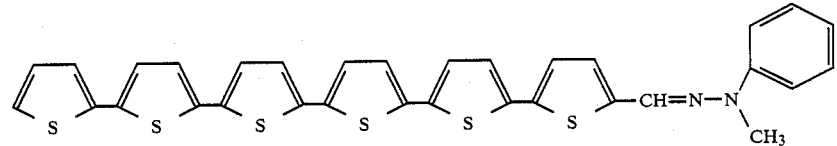
No. II-38

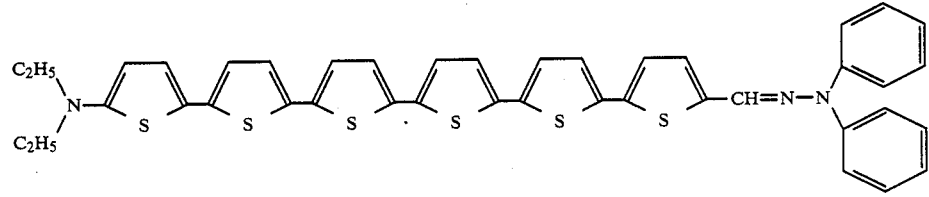
No. II-39

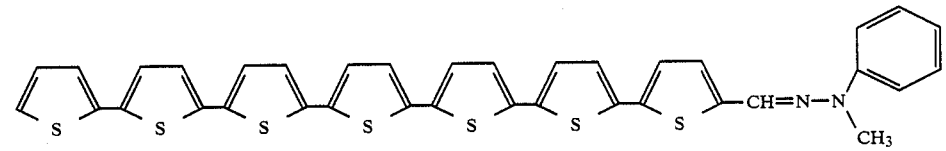
No. II-40

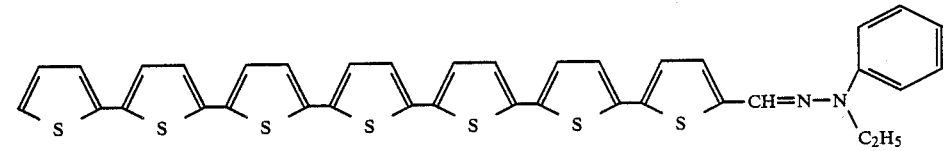
No. II-41

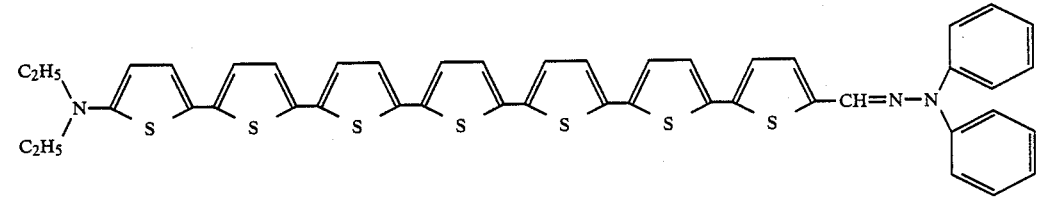
No. II-42

The example of the synthesis of such hydrazone compounds is specifically given below.

SYNTHESIS EXAMPLE 50 ml of ethanol, there were added 2.68 g of 5-formyl-(2,2'-bithiophene) and 1.68 g of 11-methyl-1-phenylhydrazine, followed by further addition of 3 drops of 1N hydrochloric acid. The mixture was refluxed for 1 hour and then cooled to room temperature. The precipitate was collected by filtration and recrystalized from ethanol to give 3.1 g of the hydrazone, i.e. the compound No. I-1 (light yellow needle-like crystal, melting point 111°–112° C.).

The compounds No. I-2 to No. I-4 were synthesized in the same manner.

The photosensitive material of the invention contains, as a charge transporting substance, a compound of general formula (I) or (II) such as mentioned above in the photosensitive layer thereof. According to the mode of use of the hydrazone compound, three embodiments of the photosensitive material a shown in FIGS. 1 to 3 are possible.

Figure 2:
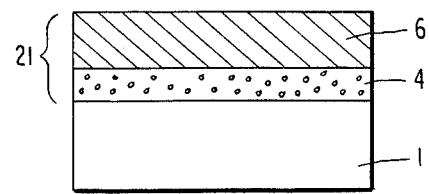
Figure 3:
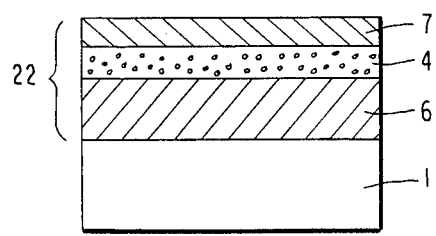

FIGS. 1 to 3 are schematic cross-sectional views of different embodiments of the photosensitive material of this invention. In the figures, the reference number 1 indicates an electroconductive substrate, 20, 21 and 22 each a photosensitive layer, 3 a charge generating substance, 4 a charge generating layer, 5 a charge transporting substance, 6 a charge transport layer, and 7 a covering layer.

In the embodiment shown in FIG. 1, a photosensitive layer 20 consisting of a dispersion of a charge generating substance 3 and a charge transporting substance 5, i.e. the hydrazone compound, in a binder resin is disposed on an electroconductive substrate 1. Such a construction is generally referred to as an integrated layer type photosensitive material.

In the embodment shown in FIG. 2, a photosensitive layer 21 which is a laminate of a charge generating layer 4 mainly composed of a charge generating substance 3 and a charge transporting substance 5 (i.e. the hydrazone compound) is disposed on an electroconductive substrate 1. Such a construction is generally referred to as an integrated layer type photosenstive material.

In the embodiment shown in FIG. 3, the layer construction is reversed as compared with that shown in FIG. 2. In the case of this construction, a covering layer 7 is generally disposed for the protection of the charge generating layer 4. The photosensitive layer 22 is composed of the charge transport layer 6, charge generating layer 4 and the covering layer 7.

The two kinds of layer construction as shown in FIG. 2 and FIG. 3 are used because the photosensitive material is used in the positive or negative charge mode. Generally, however, the layer construction shown in FIG. 2 is used in the negative charge mode. Even if it is desired to use the layer construction shown in FIG. 2 in the positive charge mode, no appropriate charge transporting substance is available at present. Therefore, for use in the positive charge mode, the layer construction shown in FIG. 3 should be employed as an effective one, as already proposed by the present inventors.

The photosensitive material shown in FIG. 1 can be prepared by dispersing a charge generating substance in a solution containing a charge transporting substance and a binder resin and applying the dispersion to an electroconductive substrate.

The photosensitive material shown in FIG. 2 can be prepared by vacuum-depositing a charge generating substance on an electroconductive substrate or by applying a dispersion of a charge generating substance in particle form in a solvent or a binder resin to an electroconductive substrate, drying the coat layer and further applying a solution containing a charge transporting substance and a binder resin onto said coat layer, followed by drying.

The photosensitive material shown in FIG. 3 can be prepared by applying a solution containing a charge transporting substance and a binder resin to an electroconductive substrate and drying, then vacuum-depositing a charge generating substance thereon or by applying a dispersion of a charge generating substance in particle form in a solvent or a binder resin and drying, and further providing a covering layer 7.

The electroconductive substrate 1 serves as an electrode of the photosensitive material and at the same time as the substrate for each layer. It may be in the form of cylinder, sheet or film and may be made of a metal such as aluminum, stainless steel or nickel or of glass, a resin or the like as electroconductively surface-treated.

As mentioned above, the charge generating layer 4 is formed by applying a dispersion of a charge generating substance 3 in particle form, in a binder resin or by the technique of vacuum vapor phase deposition or the like. Said layer 4 accepts light and generates charges. It is important that said layer have high charge generating efficiency and, at the same time, that the charges generated be injected into the charge transport layer 6 and covering layer 7. It is desirable that the injection be as little dependents as possible on the electric field and be sufficient even in low intensity electric fields Useful as the charge generating substance are metal-free phthalocyanine, titanylphthalocyanine, other phthalocyanine compounds, various azo, quinone, and indigo pigments, selenium, and selenium compounds, among others. Appropriate substances can be selected depending on the light wavelength region of the exposure light source used for image formation. The charge generating layer is only required to be capable of generating charges and, therefore, the layer thickness depends on the light absorption coefficient of the charge generating substance and generally is not more than 5 $\mu$m, preferably not more than 1 $\mu$m.

An amount of the charge generating-substance used in the present invention is selected according to a desired characteristic of the electrophotographic material, and is preferably 10 wt % or more, more preferably 20 to 100 wt %, in a charge generating layer.

It is also possible to form the charge generating layer using the charge generating substance in admixture with a minor proportion of a charge transporting substance such as hydrazones used in the present invention, oxazoles, oxadiazoles and stilbene compounds etc. and so forth. A ratio of the charge transporting substance to the charge generating substance is preferably from 0.1 to 0.8 by weight. Usable resin as the binder are polycarbonates, polyesters, polyamides, polyurethane, epoxy resins, methacrylic ester homopolymers and copolymers produced by copolymerizing a monomer derived from the above polymers with a comonomer such as stylene, methacrylate, etc., for instance, either alone or in appropriate combinations.

In the monolayer type photosensitive material, the photosensitive layer contains at least one charge generating substance in an amount of from 10 to 60 wt % based on a binder and at least one hydrazone compound in an amount of from 10 to 60 wt % based on a binder The charge transport layer 6 is a layer produced by coating on an electroconductive substrate a dispersion of the hydrazone compound of general formula (I) or (II) in a binder resin, which is to serve as a charge transporting substance. A preferable thickness of the charge transporting layer is preferably from 5 to 30 $\mu$m, and more preferably 10 to 20 $\mu$m. An amount of the charge transporting substance used in the present invention is selected according to a desired characteristic of the electrophotographic photosensitive material, and is preferably from 20 to 80 wt % in a charge transporting layer. In the dark, said layer serves as an insulator layer and retains electrostatic charges on the photosensitive material and, upon acceptance of light, transport the charges injected from the charge generating layer. Usable as the binder resin are polycarbonates, polyesters, polyamides, polyurethanes, epoxy resins, silicone resins, methacrylic ester homopolymers and copolymers, among others.

The covering layer 7, in the dark, accepts charges generated by corona discharge and retains them. It is necessary that said layer be capable of transmitting light to which the charge generating layer should respond and that said layer be capable of transmitting light at the time of exposure to thereby allow the light to reach the charge generating layer so that the surface charges can be neutralized and disappear upon injection of charges generated in the charge generating layer. Usable as the covering material are film-forming insulator materials such as polyesters and polyamides. Furthermore, such organic materials can be used in admixture with inorganic materials such as glass resins and $SiO_2$ or, further, materials which reduce the electric resistance, such as metals and metal oxides. The covering material is not limited to organic film-forming insulator materials but it is also possible to form the covering layer by using an inorganic material such as $SiO_2$ or by applying a metal, metal oxide such as Zn, Sn Ti, ZnO, $SnO_2$, $TiO_2$, etc. or the like by the technique of vapor phase deposition or sputtering, for instance. The covering material should desirably be as transparent as possible in the wavelength region corresponding to the absorption maximum of the charge generating substance.

The thickness of the covering layer may vary depending on the composition thereof but generally is optional unless the covering layer produces an adverse effect, for example causes an increase in residual potential in repeated continuous use.

The following examples are further illustrative of the present invention.

EXAMPLE I-1

A coating liquid was prepared by kneading in a mixer 50 weight parts of 50 weight parts of metal-free phthalocyanine (available from Tokyo Kasei Kogyo) pulverized beforehand in a ball mill for 150 hours, 100 weight parts of the hydrazone compound No. I-1 synthesized in the above manner, a polyester resin (Vylon; available from Toyobo Co., Ltd.) and the solvent tetrahydrofuran (THF) for 3 hours. A photosensitive layer was formed, in a dry thickness of 15 μm, on an aluminum-deposited polyester film (Al-PET) (electroconductive substrate) by applying the coating liquid to the substrate by the wire bar technique. Thus was prepared a photosensitive material.

EXAMPLE I-2

First, α-form metal-free phthalocyanine (starting material) was micropulverized in a LIMMAC (linear induction motor mixing and crushing) apparatus (Fuji Electric Co., Ltd.), where the α-form metal-free phthalocyanine was crushed in a nonmagnetic can containing Teflon pieces as working bodies, with said can disposed between two opposing linear motors, for 20 minutes. One weight parts of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the hydrazone compound No. I-1 synthesized in the above manner in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight part of the metal-free phthalocyanine treated in the above manner, 50 weight parts of a polyester resin (Vylon-200 ®; available from Toyobo Co., Ltd.), and the solvent THF for 3 hours. Thus was prepared a photosensitive material.

EXAMPLE I-3

A photosensitive material was prepared by forming a photosensitive layer in the same manner as in Example I-1 except that the composition of the charge generating layer was as follows: 50 weight parts of metal-free phthalocyanine, 100 weight parts of the hydrazone compound No.I-1, and 50 weight parts of a polyester resin (Vylon 200; Toyobo Co., Ltd.),

EXAMPLE I-4 photosensitive material was prepared by forming a photosensitive layer in the same manner as in Example I-3 except that Chlorodiane Blue, a bisazo pigment, as described in Japanese Patent Application (OPI) No. 37543/1972, was used in lieu of metal-free phthalocyanine.

The thus-obtained photosensitive materials were measured for their electrophotographic characteristics using an electrostatic recording paper testing apparatus (Kawaguchi Denki model SP-428).

The surface potential $V_s$ (volts) of each photosensitive material is the initial surface potential attained upon positively charging the photosensitive material surface by +6.0 kV corona discharging in the dark for 10 seconds. After allowing the material to stand in the dark for 2 seconds following discontinuation of the corona discharge, the surface potential $V_d$ (volts) was measured. The photosensitive material surface was then further irradiated with white light at an illuminance of 2 lux, and the time (in seconds) required for the illumination to discharge the material surface to half of $V_d$ was measured and the half decay exposure amount $E_{\frac{1}{2}}$ (lux.-Sec) was calculated. The residual potential $V_r$ (volts) is the surface potential after 10 seconds of irradiation with white light at an illuminance of 2 lux. Since the use of the phthalocyanine compound as the charge generating substance was expected to give high sensitivity to long wavelength light, the electrophotographic characteristics obtainable by the use of monochromatic light of the wavelength 780 nm were also measured. Thus, the same procedure as above was followed until Vd measurement, then 1 μW monochromatic light (780 nm) was used in lieu of white light for irradiation, and the half decay exposure amount (μJ/cm²) was determined. Further, after irradiation of the photosensitive material surface with said light for 10 seconds, the residual potential Vr (volts) was measured. The results of the measurements are in Table I-1.

TABLE I-1

| Example | White light | | | Light of wavelength 780 nm | | |
|---|---|---|---|---|---|---|
| | $V_s$ Volts | $V_r$ Volts | $E_{\frac{1}{2}}$ Lux·sec | $V_s$ Volts | $V_r$ Volts | $E_{\frac{1}{2}}$ μJ/cm$^2$ |
| I-1 | 480 | 30 | 3.5 | 450 | 25 | 1.3 |
| I-2 | 650 | 70 | 3.8 | 650 | 50 | 0.9 |
| I-3 | 600 | 65 | 3.5 | 600 | 45 | 0.85 |
| I-4 | 630 | 68 | 3.7 | — | — | — |

As can be seen in Table I-1, the photosensitive s of Examples I-1, I-2, I-3 and I-4 were comparable to one another with respect to half decay exposure and residual potential and were good also with respect to surface potential.

EXAMPLE I-5

A charge generating layer was formed on an aluminum plate having a thickness of 500 μm by vacuum deposition of selenium to a thickness of 1.5 μm. Thereon was then formed a charge transport layer by applying, with a wire bar, a coating solution prepared by mixing a solution of 100 weight parts of the hydrazone compound No. I-2 in 700 weight parts of tetrahydrofuran (THF) and a solution of 100 weight parts of polymethyl methacrylate (PMMA; Tokyo Kasei Kogyo) in 700 weight parts of toluene of give a dry layer thickness of 20 μm. When subjected to −6.0 kV corona discharge for 0.2 second, the photosensitive material obtained gave good results as follows: $V_s = -850$ V, $V_r = 60$ V, and $E_{\frac{1}{2}} = 5.1$ lux.SeC.

EXAMPLE I-6

A coating liquid was prepared by kneading in a mixer 50 weight parts of metal-free phthalocyanine treated in the same manner as in Example I-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the hydrazone compound No. I-1, 100 weight parts of a polycarbonate resin (Panlite L-1250), 0.1 weight part of a silicone oil and 700 weight parts of THF onto the charge generating layer.

When subjected to −6.0 kV corona discharge for 0.2 second in the same manner as in Example I-4, the photosensitive material obtained gave good results as follows: $V_s = -750$ V, $E_{\frac{1}{2}} = 3.2$ lux.sec.

EXAMPLE 7

A photosensitive material was prepared in the same manner as in Example I-2 except that an aluminum drum, 60 mm in outside diameter and 320 mm in length, was used as the electroconductive substrate in place of the aluminum-deposited polyester film (Al-PEPT) and that the charge transport layer (15 μm) and charge generating layer (2 μm) were formed on the exterior surface of the drum by dip coating.

The photosensitive material prepared in Example I-7 was mounted on a Carlson-system copier and evaluated by producing 100 copies successively. Good copies were obtained without image density decrease or paper sheet staining. The photosensitive material prepared in Example I-7 was mounted on the same copier, the developing section was removed, surface potentiometes were provided, and potential changes during the copying process were measured. The results thus obtained are shown in Table I-2.

TABLE I-2

| Example | Potential in the dark (volts) | | Potential in the illuminated portion (volts) | |
|---|---|---|---|---|
| | 1st copying operation | 100th copying operation | 1st copying operation | 100th copying operation |
| I-7 | 650 | 625 | 100 | 110 | both the potentials, the repeated-use characteristics were satisfactory.

EXAMPLE II-1

A coating liquid was prepared by kneading in a weight parts of 50 weight parts of metal free phthalocyanine (available from Tokyo Kasei Kogyo) pulverized beforehand in a ball mill for 150 hours, 100 weight parts of the hydrazone compound No. I-5 specified above, a polyester resin (Vylon; available from Toyobo Co., Ltd.) and the solvent tetrahydrofuran (THF) for 3 hours. A photosensitive layer was formed, in a dry thickness of 15 μm, on an aluminum-deposited polyester film (Al-PET) (electroconductive substrate) by applying the coating liquid to the substrate by the wire bar technique. Thus was prepared a photosensitive material.

EXAMPLE II-2

First, α-form metal-free phthalocyanine (starting material) was micropulverized in a LIMMAC (linear induction motor mixing and crushing) apparatus (Fuji Electric Co., Ltd.), where the u-form metal-free phthalocyanine was crushed in a nonmagnetic can containing Teflon pieces as working bodies, with said can disposed between two opposing linear motors, for 20 minutes. One weight part of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the hydrazone compound No. I-5 mentioned above in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight parts of the metal-free phthalocyanine treated in the above manner, 50 weight parts of a polyester resin (Vylon 200; available from Toyobo Co., Ltd.), and the solvent THF for 3 hours. After drying, there was obtained a photosensitive material.

EXAMPLE II-3

A photosensitive material was prepared by forming a photosensitive layer in the same manner as in Example II-1 except that the composition of the charge generating layer was as follows 50 weight parts of metal-free phthalocyanine, 100 weight parts of the hydrazone compound No. I-5, 50 weight parts of a polyester resin (Vylon 200; Toyobo Co., Ltd.) and 50 weight parts of PMMA.

EXAMPLE II-4

A photosensitive material was prepared by forming a photosensitive layer in the same manner as in Example II-3 except that Chlorodiane Blue, a bisazo pigment, was used in lieu of metal-free phthalocyanine.

The thus-obtained photosensitive materials were measured for their electrophotographic characteristics using an electrostatic recording paper testing apparatus (Kawaguchi Denki model SP-428) according to the procedure of Example I-4. The results of the measurements are shown in Table II-1.

TABLE II-1

| Example | White light | | | Light of wavelength 780 nm | | |
|---|---|---|---|---|---|---|
| | $V_s$ Volts | $V_r$ Volts | $E_{\frac{1}{2}}$ Lux·sec | $V_s$ Volts | $V_r$ Volts | $E_{\frac{1}{2}}$ μJ/cm² |
| II-1 | 475 | 25 | 3.1 | 460 | 40 | 1.1 |
| II-2 | 680 | 50 | 3.5 | 660 | 35 | 1.0 |
| II-3 | 620 | 65 | 3.8 | 600 | 30 | 0.8 |
| II-4 | 640 | 60 | 3.5 | — | — | — |

As can be seen in Table II-1, the photosensitive materials of Examples II-1, II-2, II-3 and II-4 were comparable to one another with respect to half decay exposure and residual potential and were good also with respect to surface potential.

EXAMPLE II-5

A charge generating layer was formed on an aluminum plate having a thickness of 500 μm by vacuum vapor deposition of selenium to a thickness of 1.5 μm. Thereon was then formed a charge transport layer by applying, with a wire bar, a coating solution prepared by mixing a solution of 100 weight parts of the hydrazone compound No. I-19 in 700 weight parts of tetrahydrofuran (THF) and a solution of 100 weight parts of polymethyl methacrylate (PMMA; Tokyo Kasei Kogyo) in 700 weight parts of toluene to give a dry layer thickness of 20 μm. When subjected to −6.0 kV corona discharge for 0.2 second, the photosensitive material obtained gave good results as follows: $V_S = -830$ V, $V_r = 50$ V, and $E_{\frac{1}{2}} = 4.5$ lux.sec.

EXAMPLE II-6

A coating liquid was prepared by kneading in a mixer 50 weight parts of metal-free phthalocyanine treated in the same manner as in Example II-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the hydrazone compound No. I-24, 100 weight parts of a polycarbonate resin (Panlite L-1250), 0.1 weight part of a silicone oil, 700 weight parts of THF and 700 weight parts of toluene onto the charge generating layer.

When subjected to −6.0 kV corona discharge for 0.2 second in the same manner as in Example II-4, the photosensitive material obtained gave good results as follows: $V_S = -740$ V, $E_{\frac{1}{2}} = 2.5$ lux.sec.

EXAMPLE II-7 photosensitive material was prepared in the same manner as in Example II-2 except that an aluminum drum, 60 mm in outside diameter and 320 mm in length, was used as the electroconductive substrate in place of th aluminum-deposited polyester film (Al-PET) and that the charge transport layer (15 μm) and charge generating layer (2 μm) were formed on the exterior surface of the drum by dip coating.

The photosensitive material prepared in Example II-7 was mounted on a Carlson-system copier and evaluated by producing 100 copies successively. Good copies were obtained without image density decrease or paper sheet staining. The photosensitive material prepared in Example II-7 was mounted on the same copier, the developing section was removed, surface potentiometers were provided, and potential changes during the copying process were measured. The results thus obtained are shown in Table II-2.

TABLE II-2

| Example | Potential in the dark (volts) | | Potential in the illuminated portion (volts) | |
|---|---|---|---|---|
| | 1st copying operation | 100th copying operation | 1st copying operation | 100th copying operation |
| II-7 | 640 | 620 | 100 | 110 |

As can be seen in Table II-2, the above photosensitive materials showed good repeated-use characteristics.

EXAMPLE III-1

A photosensitive material was prepared in the same way as Example I-1 except that hydrazone compound No. II-1 was used instead of the hydrazone compound No. I-5 in Example I-1.

EXAMPLE III-2

A photosensitive material was prepared in the same manner as in Example III-1 except that hydrazone compound No. II-15 was used in lieu of hydrazone compound No. II-1.

EXAMPLE III-3

A photosensitive material as is shown in FIG. 3 was prepared in the same manner as in Example II-2 except that hydrazone compound II-1 was used in lieu of hydrazone compound I-5, and the coating layer was not applied.

EXAMPLE III-4

A photosensitive material was prepared in the same manner as in Example III-3 except that the hydrazone compound No. II-15 shown hereinabove was used in place of the compound No. II-1.

EXAMPLE III-5

A photosensitive material was prepared in the same manner as in Example III-1 except that the photosensitive layer composition was as follows: 50 weight parts of metal-free phthalocyanine, 100 weight parts of the hydrazone compound No. II-1, 50 weight parts of a polyester resin (Vylon 200, Toyobo Co., Ltd.) and 50 weight parts of PMMA.

EXAMPLE III-6

A photosensitive material was prepared in the same manner as in Example III-5 except that the hydrazone compound No. II-15 was used in lieu of the compound No. II-1.

EXAMPLE III-7

A photosensitive material was prepared in the same manner as in Example III-5 except that Chlorodiane Blue, a bisazo pigment, as described in Japanese Patent Application (OPI) No. 37543/1972, was used in lieu of metal-free phthalocyanine.

EXAMPLE III-8

A photosensitive materials was prepared in the same manner as in Example III-7 except that the hydrazone compound No. II-15 was used in lieu of the copound No. II-1.

The thus-obtained photosensitive materials were measured for their electrophotographic characteristics using an electrostatic recording paper testing apparatus used in Example I-4.

The results of the measurements are shown in Table III-1.

TABLE III-1

| Example | White light | | | Light of wavelength 780 nm | | |
|---|---|---|---|---|---|---|
| | $V_s$ Volts | $V_r$ Volts | $E_{\frac{1}{2}}$ Lux·sec | $V_s$ Volts | $V_r$ Volts | $E_{\frac{1}{2}}$ μJ/cm² |
| III-1 | 650 | 90 | 4.3 | 680 | 100 | 4.9 |
| III-2 | 700 | 100 | 5.1 | 710 | 80 | 3.8 |
| III-3 | 720 | 100 | 4.8 | 730 | 80 | 4.1 |
| III-4 | 780 | 80 | 4.3 | 740 | 60 | 4.5 |
| III-5 | 750 | 50 | 4.2 | 720 | 70 | 4.5 |
| III-6 | 730 | 70 | 4.8 | 750 | 70 | 4.6 |
| III-7 | 680 | 100 | 5.3 | — | — | — |
| III-8 | 750 | 80 | 5.0 | — | — | — |

As can be seen in Table III-1, the photosensitive materials of Examples III-1 to III-8 in which the hydrazone compound No. II-1 or II-15 was used as the charge transporting substance were satisfactory with respect to surface potential $V_s$, half decay exposure amount $E_{\frac{1}{2}}$ and residual potential $V_r$. The photosensitive materials of Examples III-1 to III-6 in which the phthalocyanine compound was used as the charge generating substance showed good electrophotographic characteristics also against the long wavelength (780 nm) light.

EXAMPLE III-9

A photosensitive material as is shown in FIG. 2 was prepared in the same manner as in Example I-5 except that the hydrazone compound No. II-2 instead of the hydrazone compound No. I-2.

The photosensitive material was subjected to -6.0 KV corona discharge in for 2 seconds and then electrophotographic characteristics were measured to oprov good results as follows:

$$V_s = -880 \text{ V}, V_r = -100\text{V}, E_{\frac{1}{2}} = 5.1 \text{ lux. sec.}$$

EXAMPLE III-10

A photosensitive material was prepared in the same manner as in Example III-9 except that the hydrazone compound No. II-16 was used in stead of the compound No. II-2. The photosensitive material was measured for its characteristics and gave good results as follows:

$$V_s = -780 \text{ V}, V_r = -60 \text{ V}, E_{\frac{1}{2}} = 3.8 \text{ lux. sec.}$$

EXAMPLE III-11

A coating liquid was prepared by kneading in a mixer 50 weight parts of metal-free phthalocyanine treated in the same manner as in Example II-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the hydrazone compound No. II-3, 100 weight parts of a polycarbonate resin (Panlite L-1250), 0.1 weight part of a silicone oil, 700 weight parts of THF and 700 weight parts of toluene onto the charge generating layer.

When subjected to −6.0 kV corona discharge for 0.2 second in the same manner as in Example III-9, the photosensitive material obtained gave good results as follows: $V_s = -850$ V, $E_{\frac{1}{2}} = 5.5$ lux.sec.

EXAMPLE III-12

A photosensitive material was prepared in the same manner as in Example III-11 except that the hydrazone compound No. II-17 was used in lieu of the compound No. II-3. The photosensitive material was measured for its characteristics and gave good results as follows:

$$V_s = -800 \text{ V}, E_{\frac{1}{2}} = 4.2 \text{ lux.sec.}$$

EXAMPLE III-13

Photosensitive materials having the construction shown in FIG. 1 were prepared by forming a photosensitive layer in the same manner as in Example III-7 except that the hydrazone compounds Nos. II-4 to II-14 were used in lieu of the compound No. II-1. They were measured for electrophotographic characteristics in the same manner as in Example III-8. The photosensitive materials were subjected to +6.0 kV corona discharge in the dark for 10 seconds and then illuminated with white light at an illuminance of 2 lux. The half decay exposure data ($E_{\frac{1}{2}}$) thus obtained are shown in Table III-2.

TABLE III-2

| Compound No. | $E_{\frac{1}{2}}$ (lux · sec) |
|---|---|
| II-4 | 4.8 |
| II-5 | 3.9 |
| II-6 | 4.5 |
| II-7 | 5.0 |
| II-8 | 5.3 |
| II-9 | 4.8 |
| II-10 | 4.3 |
| II-11 | 4.1 |
| II-12 | 5.3 |
| II-13 | 5.1 |
| II-14 | 4.9 |

As can be seen in Table III-2, also the photosensitive materials with the hydrazone compounds Nos. III-4 to III-14 each as the charge transporting substance were found to be highly sensitive, giving good half decay exposure data.

EXAMPLE III-14

Photosensitive materials were prepared in the same manner as in Example III-7 except that the hydrazone compounds. Nos. II-18 to II-42 specifically shown hereinabove were used in lieu of the hydrazone compound No. II-1. They were measured for electrophotographic characteristics in the same manner as in Example III-13.

Among the measurement results, the half decay exposure data alone are shown in Table III-3.

TABLE III-3

| Compound No. | $E_{\frac{1}{2}}$ (lux · sec) |
| --- | --- |
| II-18 | 4.5 |
| II-19 | 5.2 |
| II-20 | 3.8 |
| II-21 | 5.5 |
| II-22 | 4.8 |
| II-23 | 4.7 |
| II-24 | 4.2 |
| II-25 | 4.6 |
| II-26 | 5.0 |
| II-27 | 5.5 |
| II-28 | 6.0 |
| II-29 | 3.9 |
| II-30 | 4.3 |
| II-31 | 4.1 |
| II-32 | 4.3 |
| II-33 | 5.0 |
| II-34 | 4.2 |
| II-35 | 4.8 |
| II-36 | 4.7 |
| II-37 | 4.1 |
| II-38 | 4.5 |
| II-39 | 5.0 |
| II-40 | 5.3 |
| II-41 | 4.9 |
| II-42 | 5.2 |

As can be seen in Table III-3, the photosensitive materials obtained by using the hydrazone compounds Nos. II-18 to II-42 each as the charge transporting substance gave good half decay exposure data and were found to be highly sensitive.

As mentioned hereinabove, the use, in accordance with the invention, of the above-mentioned hydrazone compounds of general formulas (I) and (II) results in photosensitive materials having high sensitivity in the positive as well as in the negative charge mode of use and having excellent repeated-use characteristics. The charge generating substance can be selected so that it can fit to the exposure light source to be used. Thus, for instance, it is possible to obtain photosensitive materials usable in semiconductor laser printers by using phthalocyanine and/or a certain kind of bisazo compound. The durability of said materials can be improved by providing a covering layer on the surface thereof.

While the invention has been described in detail and with reference to specific embodiments thereof, it will be apparent to one skilled in the art that various changes and modification can be made therein without departing from the spirit and scope thereof.

What is claimed is:

1. An electrophotographic photosensitive material comprising a photosensitive layer containing at least one hydrazone compound selected from the group consisting of compounds having the general formulae (I) and (II):

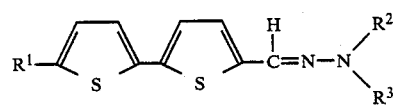

wherein $R^1$ is a hydrogen or halogen atom or an alkyl group, an alkoxy group, a nitro group, an acyl group or an amino group and $R^2$ and $R^3$ each represents a substituted or unsubstituted alkyl group, or a substituted or unsubstituted aryl group;

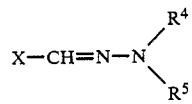

wherein $R^4$ and $R^5$ each represents a substituted or unsubstituted alkyl group, or a substituted or unsubstituted aryl group and X is a group of the formula

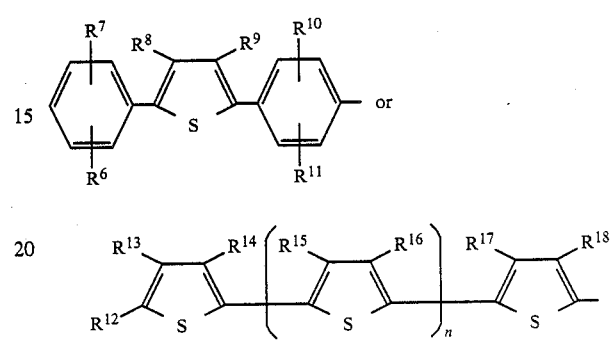

in which $R^6$ to $R^{18}$ each represents a hydrogen or halogen atom or a hydroxy group, an alkyl group, an alkoxy group, an allyl group, an acyl group, an acyloxy group, an alkoxycarbonyl group, an aryl group, a cyano group, a nitro group, an amino group, an alkylamino group or an arylamino group and n is an integer of 1, 2, 3, 4 or 5.

2. A electrophotographic photosensitive material as claimed in claim 1, wherein in the formula (I), the alkyl group represented by $R^1$ has from 1 to 10 carbon atoms, the alkoxy group represented by $R^1$ has from 1 to 10 carbon atoms, the amino group represented by $R^1$ has from 0 to 10 carbon atoms, and the acyl group represented by $R^1$ has from 1 to 6 carbon atoms, and the alkyl group represented by $R^2$ and $R^3$ has from 1 to 10 carbon atoms and the aryl group represented by $R^2$ and $R^3$ has from 6 to 12 carbon atoms.

3. The electrophotographic photosensitive material as claimed in claim 1, wherein in the formula (II), the alkyl group represented by $R^4$ and $R^5$ has from 1 to 10 carbon atoms, and the aryl group represented by $R^4$ and $R^5$ has from 6 to 12 carbon atoms, and the alkyl group represented by $R^6$ to $R^{18}$ has from 1 to 10 carbon atoms, the alkoxy group represented by $R^6$ to $R^{18}$ has from 1 to 10 carbon atoms, the acyl group represented by $R^6$ to $R^{18}$ has from 1 to 10 carbon atoms, the acyloxy group represented by $R^6$ to $R^{18}$ has from 1 to 10 carbon atoms, the aryl group represented by $R^6$ to $R^{18}$ has from 1 to 10 carbon atoms, the alkoxycarbonyl group represented by $R^6$ to $R^{18}$ has from 2 to 10 carbon atoms, the alkylamino group represented by $R^6$ to $R^{18}$ has from 1 to 10 carbon atoms, and the arylamino group represented by $R^6$ to $R^{18}$ has from 6 to 12 carbon atoms.

4. An electrophotographic photosensitive material as claimed in claim 1, wherein the formula (I), $R^1$ represents a hydrogen atom, a halogen atom, a methyl group, a nitro group, an acetyl group or an amino group, and $R^2$ and $R^3$ each represents a methyl group, an ethyl group, a methoxyphenyl group, a phenyl group, a naphthyl group, a methylphenyl group or a chlorophenyl group.

5. An electrophotographic photosensitive material as claimed in claim 1, wherein in the formula (II), $R^4$ and $R^5$ each represents a methyl group, and ethyl group, a phenyl group, a benzyl group, a methylphenyl group, a methoxyphenyl group, a naphthyl group, and $R^6$ to $R^{18}$ each represents a hydrogen atom, a methyl group, a halogen atom, an ethyl group, an a phenyl group, a nitro group, an amino group, a methoxy group, a diethylamino group or an acetyl group.

6. An electrophotographic photosensitive material as claimed in claim 1, wherein the photosensitive layer consists of a single layer containing both the charge generating substance and at least one hydrazone compound selected from the group consisting of the compounds represented by the formulae (I) and (II) claimed in claim 1.

7. An electrophotographic photosensitive material as claimed in claim 1, wherein the photosensitive layer consists of the combination of a charge generating layer containing the charge generating substance and a charge transporting layer containing at least one hydrazone compound selected from the group consisting of the compounds represented by the formulae (I) and (II) claimed in claim 1.

8. An electrophotographic photosensitive material as claimed in claim 6, wherein the proportion of the hydrazone compound claimed in claim 1 in the photosensitive layer is contained in an amount of 10 to 60 wt % with respect to the binder, and further wherein the proportion of the charge generating substance in the photosensitive layer is 10 to 60 wt % with respect to the binder.

9. An electrophotographic photosensitive material as claimed in claim 7, wherein the proportion of the hydrazone compound claimed in claim 1 in the charge transporting layer is 20 to 80 wt % with respect to the charge transporting layer.

* * * * *